United States Patent
Hashida et al.

(10) Patent No.: US 10,551,364 B2
(45) Date of Patent: Feb. 4, 2020

(54) CONTROL SYSTEM AND CONTROL METHOD FOR INTERNAL COMBUSTION ENGINE

(71) Applicant: TOYOTA JIDOSHA KABUSHIKI KAISHA, Toyota-shi, Aichi-ken (JP)

(72) Inventors: Tatsuhiro Hashida, Shizuoka-ken (JP); Kazuhiro Wakao, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 327 days.

(21) Appl. No.: 14/894,848

(22) PCT Filed: Feb. 16, 2015

(86) PCT No.: PCT/IB2015/000157
§ 371 (c)(1),
(2) Date: Nov. 30, 2015

(87) PCT Pub. No.: WO2015/124984
PCT Pub. Date: Aug. 27, 2015

(65) Prior Publication Data
US 2016/0349206 A1    Dec. 1, 2016

(30) Foreign Application Priority Data
Feb. 20, 2014 (JP) .................... 2014-030968

(51) Int. Cl.
*G01N 27/407*    (2006.01)
*G01N 33/00*    (2006.01)
(Continued)

(52) U.S. Cl.
CPC ..... *G01N 33/0042* (2013.01); *F02D 41/1444* (2013.01); *F02D 41/1454* (2013.01);
(Continued)

(58) Field of Classification Search
CPC ............ G01N 27/4074; G01N 27/409; G01N 33/0036; G01N 33/0042; F01N 2560/027
(Continued)

(56) References Cited

U.S. PATENT DOCUMENTS

| | | | |
|---|---|---|---|
| 5,145,566 A | | 9/1992 | Logothetis et al. |
| 5,554,269 A | * | 9/1996 | Joseph ............... G01N 27/4065 204/424 |

(Continued)

FOREIGN PATENT DOCUMENTS

| | | |
|---|---|---|
| EP | 0361692 A2 | 4/1990 |
| JP | S5647751 A * | 4/1981 ........... G01N 27/416 |

(Continued)

OTHER PUBLICATIONS

U.S. Patent and Trademark Office, Office Action issued to U.S. Appl. No. 14/912,786 dated Aug. 10, 2017, 22 pages.

(Continued)

*Primary Examiner* — Kevin R Steckbauer
(74) *Attorney, Agent, or Firm* — Hunton Andrews Kurth LLP

(57) ABSTRACT

A control system for an engine including a limiting current sensor, the control system includes an ECU configured to: execute a sweep process for gradually reducing a voltage that is applied to the sensor from a first voltage a second voltage; acquire an extreme value of an output current of the sensor during execution of the sweep process from output currents of the sensor while a voltage included in a specific voltage range is applied to the sensor, the extreme value being predicted to be output; and detect the concentration of SOx in exhaust gas based on the extreme value and a reference value, the reference value being a value of limiting (Continued)

current of the sensor, the value of limiting current of the sensor corresponding to the concentration of oxygen having the constant value.

5 Claims, 10 Drawing Sheets

(51) Int. Cl.
*F02D 41/14* (2006.01)
*F01N 13/00* (2010.01)
(52) U.S. Cl.
CPC ........ *G01N 27/4074* (2013.01); *F01N 13/008* (2013.01); *F01N 2560/027* (2013.01); *Y02A 50/248* (2018.01)
(58) Field of Classification Search
USPC .................. 60/276; 123/703; 73/114.71
See application file for complete search history.

(56) References Cited

U.S. PATENT DOCUMENTS

| | | | | |
|---|---|---|---|---|
| 5,667,652 | A * | 9/1997 | Liu | G01N 27/4074 204/412 |
| 6,051,123 | A * | 4/2000 | Joshi | G01N 27/4075 204/412 |
| 6,716,327 | B1 * | 4/2004 | De La Prieta | G01N 27/4074 204/415 |
| 8,707,677 | B2 | 4/2014 | Kowalkowski et al. | |
| 8,875,560 | B2 * | 11/2014 | Korenev | F01N 11/00 73/31.05 |
| 2002/0157379 | A1 | 10/2002 | Kakuyama et al. | |
| 2002/0173919 | A1 | 11/2002 | Moteki et al. | |
| 2005/0040041 | A1 | 2/2005 | Sakayanagi | |
| 2012/0117942 | A1 | 5/2012 | Kowalkowski et al. | |
| 2013/0000377 | A1 * | 1/2013 | Korenev | G01N 33/0006 73/1.06 |
| 2013/0000386 | A1 * | 1/2013 | Korenev | G01M 15/00 73/31.05 |
| 2014/0116031 | A1 | 5/2014 | Yoshida et al. | |
| 2016/0208721 | A1 | 7/2016 | Wakimoto et al. | |

FOREIGN PATENT DOCUMENTS

| | | |
|---|---|---|
| JP | H02-122255 A | 5/1990 |
| JP | H03-100454 A | 4/1991 |
| JP | 2002-349250 A | 12/2002 |
| JP | 2008-076410 A | 4/2008 |
| JP | 2015-017931 A | 1/2015 |
| JP | 2015-017932 A | 1/2015 |
| JP | 2015-036538 A | 2/2015 |
| JP | 2015-040546 A | 3/2015 |
| JP | 2015-155665 | 8/2015 |
| WO | 2013/021703 A1 | 2/2013 |
| WO | 2015/022568 A1 | 2/2015 |
| WO | 2015/025202 A1 | 2/2015 |

OTHER PUBLICATIONS

U.S. Patent and Trademark Office, Notice of Allowance issued to U.S. Appl. No. 14/912,786 dated Jan. 10, 2018, 11 pages.

* cited by examiner

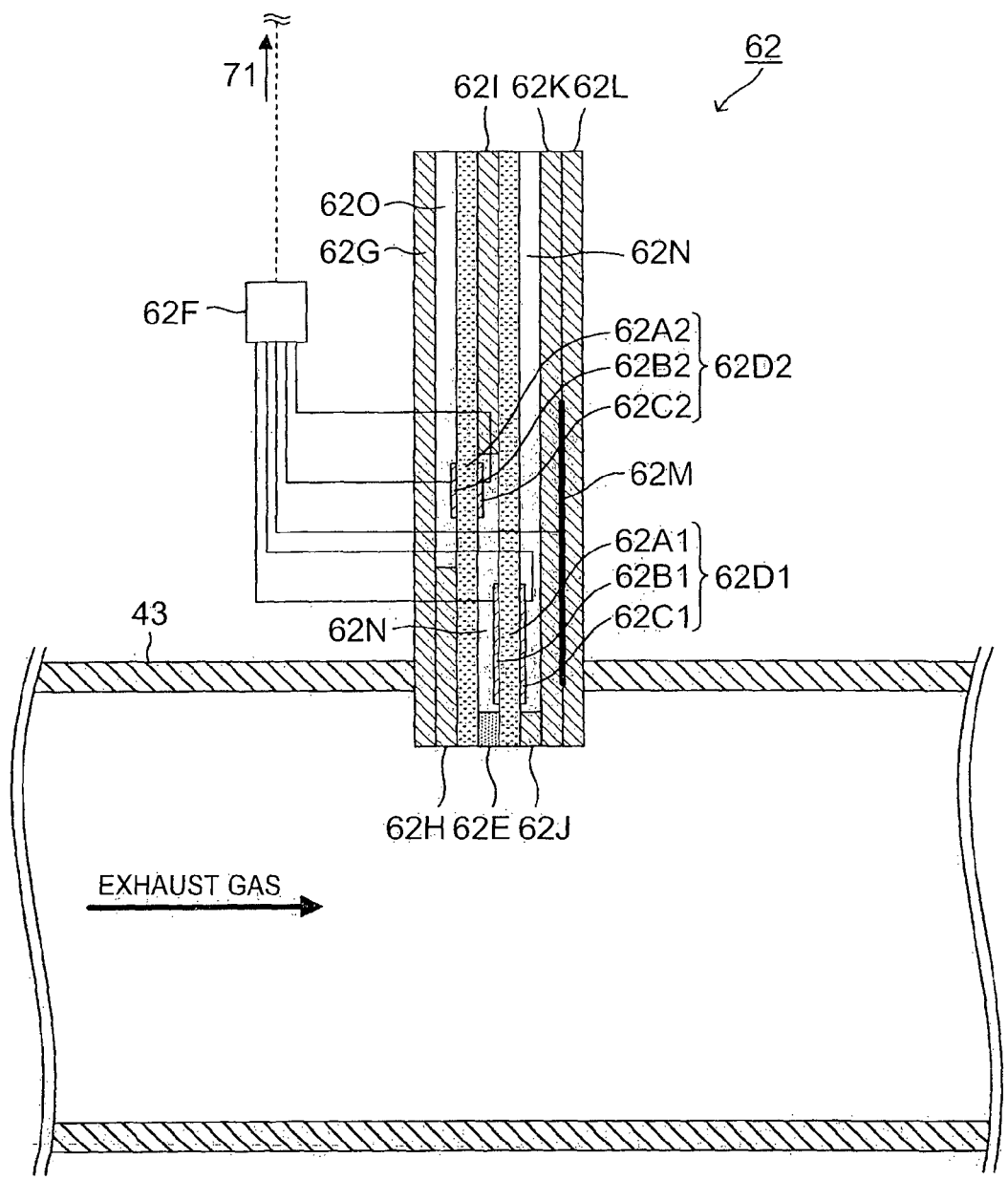

CONTROL SYSTEM AND CONTROL METHOD FOR INTERNAL COMBUSTION ENGINE

CROSS-REFERENCE TO RELATED APPLICATIONS

This is a national phase application based on the PCT International Patent Application No. PCT/IB2015/000157 filed Feb. 16, 2015, claiming priority to Japanese Patent Application No. 2014-030968 filed Feb. 20, 2014, the entire contents of both of which are incorporated herein by reference.

BACKGROUND OF THE INVENTION

1. Field of the Invention

The invention relates to a control system and control method for an internal combustion engine, which detect the concentration of SOx in exhaust gas with the use of a limiting current sensor that is able to detect the concentration of oxygen in exhaust gas from the internal combustion engine.

2. Description of Related Art

As a sensor that detects the concentration of oxygen in exhaust gas, there is known a limiting current sensor including a solid electrolyte, a pair of electrodes (an electrode pair formed of a measuring electrode and a reference electrode) and a diffusion-controlling layer (diffusion resistance layer). The solid electrolyte is able to conduct oxygen ions. The pair of electrodes are provided so as to sandwich the solid electrolyte. The diffusion-controlling layer is provided so as to cover the measuring electrode.

The principle of detecting the concentration of oxygen in exhaust gas with the use of the above sensor is as follows. Initially, when a voltage is applied to the electrode pair so that a predetermined potential difference is generated between the electrode pair, oxygen in exhaust gas is ionized at the measuring electrode. Oxygen ions pass through the solid electrolyte and migrate to the reference electrode, and then return into oxygen at the reference electrode through recombination. Migration of electrons due to the series of electrochemical reactions is output as a current from the electrode pair. Because the diffusion-controlling layer is controlling migration of oxygen to the measuring electrode, the magnitude of current that is output from the electrode pair is in a one-to-one correspondence with the concentration of oxygen in exhaust gas. Thus, when a current that is output from the electrode pair is measured, the concentration of oxygen in exhaust gas is identified (detected) on the basis of the measured current.

As one of such detecting devices, there is a detecting device that detects the concentration of a component other than oxygen (for example, the concentration of $H_2O$, that is, humidity) by utilizing the fact that a molecular that is decomposed at the measuring electrode varies as the magnitude of voltage that is applied to the electrode pair varies. Specifically, the detecting device uses a sensor having two sets of electrode pair (an upstream-side electrode pair and a downstream-side electrode pair). The detecting device initially applies a voltage having a magnitude of decomposing oxygen to the upstream-side electrode pair, and emits oxygen in exhaust gas to the outside of the sensor. Subsequently, the detecting device applies a voltage having a magnitude of decomposing $H_2O$ to the downstream-side electrode pair, and measures a current that is output from the downstream-side electrode pair. The detecting device identifies the concentration of $H_2O$ in exhaust gas on the basis of the current. Thus, the detecting device is able to measure a current that is output because of $H_2O$ as distinguished from a current that is output because of oxygen, so it is possible to accurately detect the concentration of $H_2O$ (see, for example, Japanese Patent Application Publication No. 2-122255 (JP 2-122255 A)).

Hereinafter, the limiting current sensor that is able to detect the concentration of oxygen in exhaust gas is referred to as oxygen concentration sensor, the voltage that is applied to the electrode pair of the sensor is referred to as applied voltage to the sensor, and the current that is output from the electrode pair is referred to as output current of the sensor. The internal combustion engine is referred to as engine.

The amount of sulfur component contained in fuel for the engine is generally an extremely small amount. However, depending on a region, or the like, in which the engine is used, fuel having a relatively high concentration of sulfur may be used. In this case, sulfur oxides (SOx) that are produced during combustion can cause white smoke, or the like, of exhaust gas. Therefore, it is desired to measure the concentration of sulfur in fuel. The inventors of the invention have studied that the concentration of SOx in exhaust gas is detected as a parameter related to the concentration of sulfur in fuel.

Specifically, the inventors of the invention have studied whether it is possible to detect the concentration of SOx in exhaust gas by using the method employed in the above-described detecting device. As a result of the study, it has been found that, when a voltage having a magnitude of decomposing SOx (in other words, reducing SOx into sulfur) is applied to the electrode pair of the oxygen concentration sensor, not only SOx but also a component other than SOx in exhaust gas also decomposes, and it has been found that it is not easy to measure only an output current due to SOx separately. That is, with the method employed in the existing device, there is a case where it is difficult to accurately detect the concentration of SOx in exhaust gas.

SUMMARY OF THE INVENTION

The invention provides a control system and a control method that are able to accurately detect the concentration of SOx in exhaust gas from an engine.

A first aspect of the invention provides a control system for an internal combustion engine including a limiting current sensor that is able to detect a concentration of oxygen in exhaust gas. The control system includes an electronic control unit configured to: (i) detect a concentration of SOx in exhaust gas; (ii) control the engine such that the concentration of oxygen in exhaust gas is kept at a constant value; (iii) execute a sweep process for gradually reducing a voltage, the voltage being applied to the sensor from a first voltage to a second voltage, sulfur being produced as a result of reduction of SOx in the sensor and being accumulated in the sensor at the first voltage, sulfur in the sensor being oxidized into SOx at the second voltage; (iv) acquire an extreme value of an output current of the sensor during execution of the sweep process from output currents of the sensor while a voltage included in a specific voltage range is applied to the sensor, the extreme value being predicted to be output based on the concentration of oxygen having the constant value in the specific voltage range; and (v) detect the concentration of SOx in exhaust gas based on the extreme value and a reference value, the reference value being a value of limiting current of the sensor, the value of limiting current of the sensor corresponding to the concentration of oxygen having the constant value.

According to the experiment and consideration of the inventors of the invention, the following findings are obtained. When the sweep process is executed, the output current of the sensor includes an output component due to reoxidation of sulfur, accumulated in the sensor, into SOx (that is, an output component due to the concentration of SOx) and an output component due to the concentration of oxygen. However, the output current does not substantially include an output component due to another component. Thus, when the sweep process is executed under control, in which the concentration of oxygen in exhaust gas is kept at a constant value, the output current draws the waveform corresponding to the concentration of SOx. Specifically, the output current under the control has an extreme value (a peak value of output current) that changes with the concentration of SOx. When the extreme value is compared with the output component (that is, the reference value) due to the concentration of oxygen having the constant value, it is possible to detect the concentration of SOx. The applied voltage to the sensor at the time when the extreme value is output changes with the concentration of oxygen during execution of the sweep process (that is, the concentration of oxygen having the constant value). Thus, it is possible to determine the range of the applied voltage in which an extreme value is predicted to be output (that is, the specific voltage range) on the basis of the concentration of oxygen having the constant value.

Therefore, the system according to the invention executes the sweep process under control that is executed so that the concentration of oxygen in exhaust gas is kept at the constant value, and the extreme value is acquired on the basis of output currents in the specific voltage range, the extreme value being predicted to be output on the basis of the concentration of oxygen having the constant value in the specific voltage range. Thus, even under an environment that unintended noise, or the like, is added to the output current of the sensor, the system according to the invention is able to acquire the extreme value by ignoring noise, or the like, outside the specific voltage range. The system according to the invention detects the concentration of SOx in exhaust gas on the basis of the extreme value and the reference value. As a result, while the system according to the invention prevents erroneous measurement due to noise, or the like, as much as possible, the system is able to detect the concentration of SOx by measuring (acquiring) only the output component due to the concentration of SOx (extreme value) as distinguished from the output currents.

Thus, the thus configured system according to the invention is able to accurately detect the concentration of SOx in exhaust gas.

As described above, the system according to the invention acquires the output component due to the concentration of SOx (the extreme value of output current) in process of detecting the concentration of SOx in exhaust gas. The output component is in a one-to-one correspondence with the concentration of SOx, so the output component substantially indicates the concentration of SOx. Therefore, the concentration of SOx in the invention can translate to at least one of the concentration of SOx in exhaust gas or a value that is in a one-to-one correspondence with the concentration of SOx.

The specific voltage range can translate to a voltage range that includes a specific applied voltage (specific value) at which the output current of the sensor is predicted to reach the extreme value. The specific voltage range includes that the width of the range is zero (in other words, a voltage included in the specific voltage range is only the specific value). When the width of the specific voltage range is zero, the extreme value of output current corresponds to the value of output current at the time when the applied voltage is the specific value.

In addition, detection of the concentration of SOx can be, for example, carried out so that the concentration of SOx increases as the absolute value of the difference between the extreme value and the reference value increases. With this system, it is possible to detect the concentration of SOx in exhaust gas without requiring complicated calculation. The correlation between the absolute value of the difference between the extreme value and the reference value and the concentration of SOx in exhaust gas can be determined by an experiment, or the like, in advance.

The system according to the invention does not simply measure the output current for each applied voltage. The system is able to measure only an output current component (extreme value) due to SOx in exhaust gas separately through the specific process according to the invention called sweep process. As a result, the system according to the invention is able to accurately detect the concentration of SOx in exhaust gas.

The reference value may be acquired when the sweep process is actually executed or may be acquired by consulting a map, or the like, determined in advance through an experiment, or the like.

In the case where the reference value is acquired when the sweep process is actually executed, if the timing of acquiring the reference value and the timing of executing the sweep process are excessively apart from each other, there is a possibility that the detection accuracy of the concentration of SOx decreases, for example, if the output characteristic of the sensor has changed with time. Therefore, in order to accurately detect the concentration of SOx as much as possible, it is desirable that the timing of acquiring the reference value and the timing of executing the sweep process be close to each other as much as possible.

In the above control system, the second voltage may coincide with a voltage that is used when the concentration of oxygen in exhaust gas is detected, and the electronic control unit may be configured to, as the reference value, use a value of output current of the sensor at timing at which the voltage that is applied to the sensor is reduced to the second voltage in the sweep process.

According to the experiment, and the like, of the inventors, when the sweep process is executed, usually, reoxidation of all the sulfur accumulated in the sensor completes before the second voltage reaches the applied voltage that is used at the time when the concentration of oxygen in exhaust gas is detected. Therefore, although the second voltage itself is a voltage at which oxidation of sulfur can occur, the output current at the time when the applied voltage is the second voltage usually includes only the output component due to oxygen.

Therefore, the system according to the aspect, as the reference value, uses the output current at the timing at which the applied voltage has decreased to the second voltage. The system according to the aspect acquires the reference value at the timing at which the sweep process has completed, so acquiring the reference value and executing the sweep process are substantially successively carried out. Thus, the system according to the aspect is able to further accurately detect the concentration of SOx in exhaust gas in comparison with the case where the timing of acquiring the reference value and the timing of executing the sweep process are apart from each other.

On the other hand, in the case where the reference value is acquired by consulting a map, or the like, determined in advance through an experiment, or the like, that is, for example, the correlation between the concentration of oxygen and the limiting current, which is prepared for measuring the concentration of oxygen, may be utilized.

In the above control system, the electronic control unit may be configured to prestore a correlation between the concentration of oxygen in exhaust gas and the value of limiting current, and the electronic control unit may be configured to, as the reference value, use a value of limiting current, which is obtained by applying the concentration of oxygen having the constant value to the correlation.

With the above configuration, although it is required to acquire the concentration of oxygen in exhaust gas (constant value) during the sweep process, it is not required to separately carry out measurement, or the like, for determining the reference value. Thus, the system according to the aspect is able to simply and quickly detect the concentration of SOx. Because the correlation is prestored, the system according to the aspect is able to reliably determine the reference value even when the concentration of oxygen in exhaust gas (constant value) during the sweep process varies for the concentration of SOx.

In terms of the above-described principle of detecting the concentration of SOx, the second voltage just needs to be the applied voltage lower than the applied voltage at which the extreme value is output from the sensor.

In the above control system, the second voltage may coincide with a lower limit value of the specific voltage range.

With the above configuration, because a period during which the sweep process is executed (that is, a period during which the concentration of oxygen in exhaust gas is kept at the constant value) is prevented from extending more than necessary, it is possible to reduce the influence of detection of the concentration of SOx on operation of the internal combustion engine.

A second aspect of the invention provides a control method for an internal combustion engine including a limiting current sensor that is able to detect a concentration of oxygen in exhaust gas. The control method includes: detecting a concentration of SOx in exhaust gas; controlling the engine such that the concentration of oxygen in exhaust gas is kept at a constant value; executing a sweep process for gradually reducing a voltage, the voltage being applied to the sensor from a first voltage to a second voltage, sulfur being produced as a result of reduction of SOx in the sensor and being accumulated in the sensor at the first voltage, sulfur in the sensor being oxidized into SOx at the second voltage; acquiring an extreme value of an output current of the sensor during execution of the sweep process from output currents of the sensor while a voltage included in a specific voltage range is applied to the sensor, the extreme value being predicted to be output based on the concentration of oxygen having the constant value in the specific voltage range; and detecting the concentration of SOx in exhaust gas based on the extreme value and a reference value, the reference value being a value of limiting current of the sensor, the value of limiting current of the sensor corresponding to the concentration of oxygen having the constant value.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 11 is a schematic view that shows the schematic configuration of a limiting current oxygen concentration sensor (dual-cell sensor) according to the embodiment.

DETAILED DESCRIPTION OF EMBODIMENTS

Figure 1:
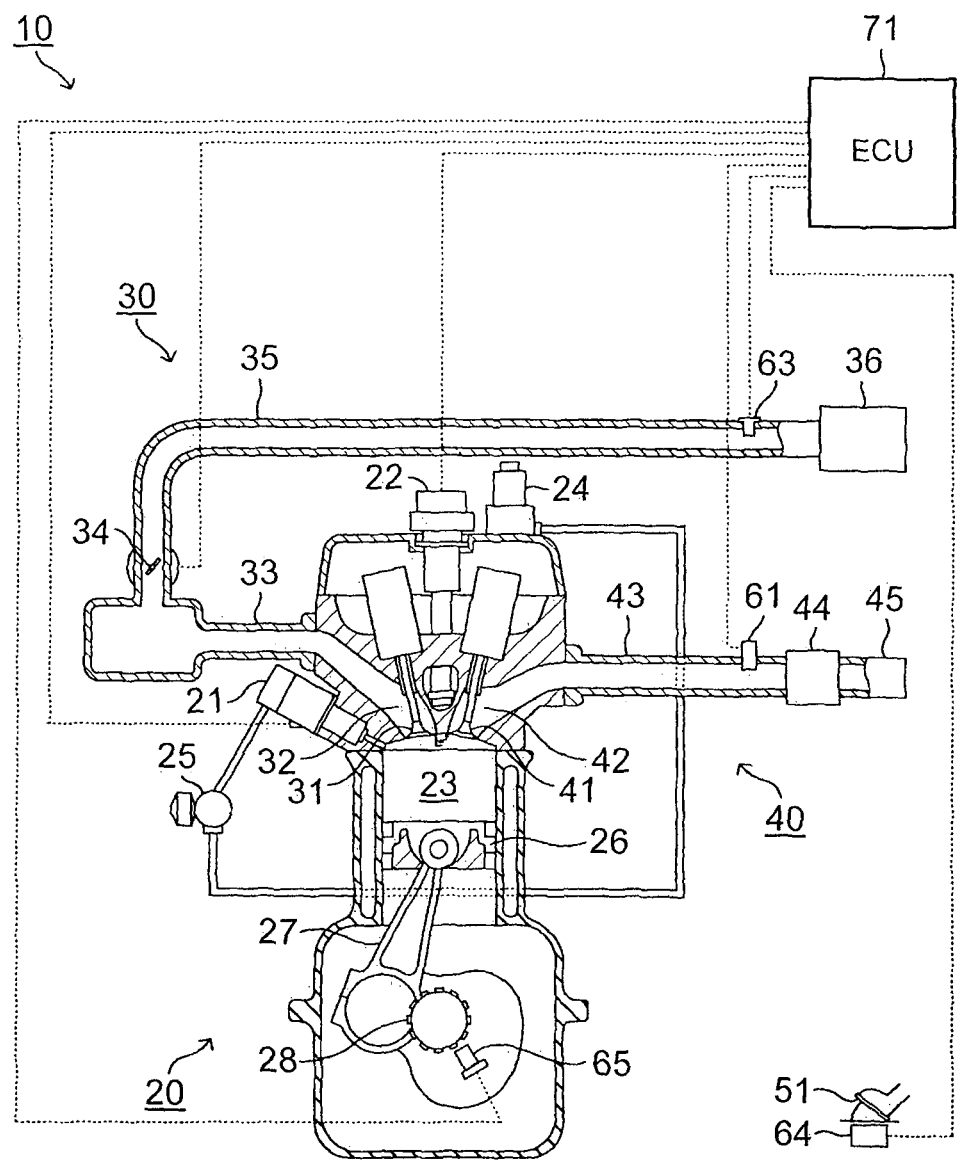
FIG. 1 is a schematic view that shows the schematic configuration of an internal combustion engine to which a control system according to an embodiment of the invention is applied.

FIG. 1 shows the schematic configuration of an internal combustion engine 10 to which a control system according to an embodiment of the invention (hereinafter, referred to as embodied system) is applied.

The engine 10 is a spark ignition internal combustion engine (so-called gasoline engine). The engine 10 includes a body portion 20, an intake system 30, an exhaust system 40, an accelerator pedal 51, a plurality of sensors 61 to 64, and an electronic control unit 71. The body portion 20 includes a fuel injection valve 21, an ignition plug 22, a combustion chamber 23, a fuel pump 24, a fuel supply tube 25, a piston 26, a connecting rod 27 and a crankshaft 28. The intake system 30 includes an intake valve 31, an intake port 32, an intake manifold 33, a throttle valve 34, an intake pipe 35 and an air cleaner 36. The exhaust system 40 includes an exhaust valve 41, an exhaust port 42, an exhaust manifold 43, an exhaust gas purification catalyst 44 and an exhaust pipe 45. The plurality of sensors 61 to 64 include a limiting current oxygen concentration sensor 61, a crank position sensor 65, an air flow meter 63 and an accelerator operation amount sensor 64.

Figure 2:
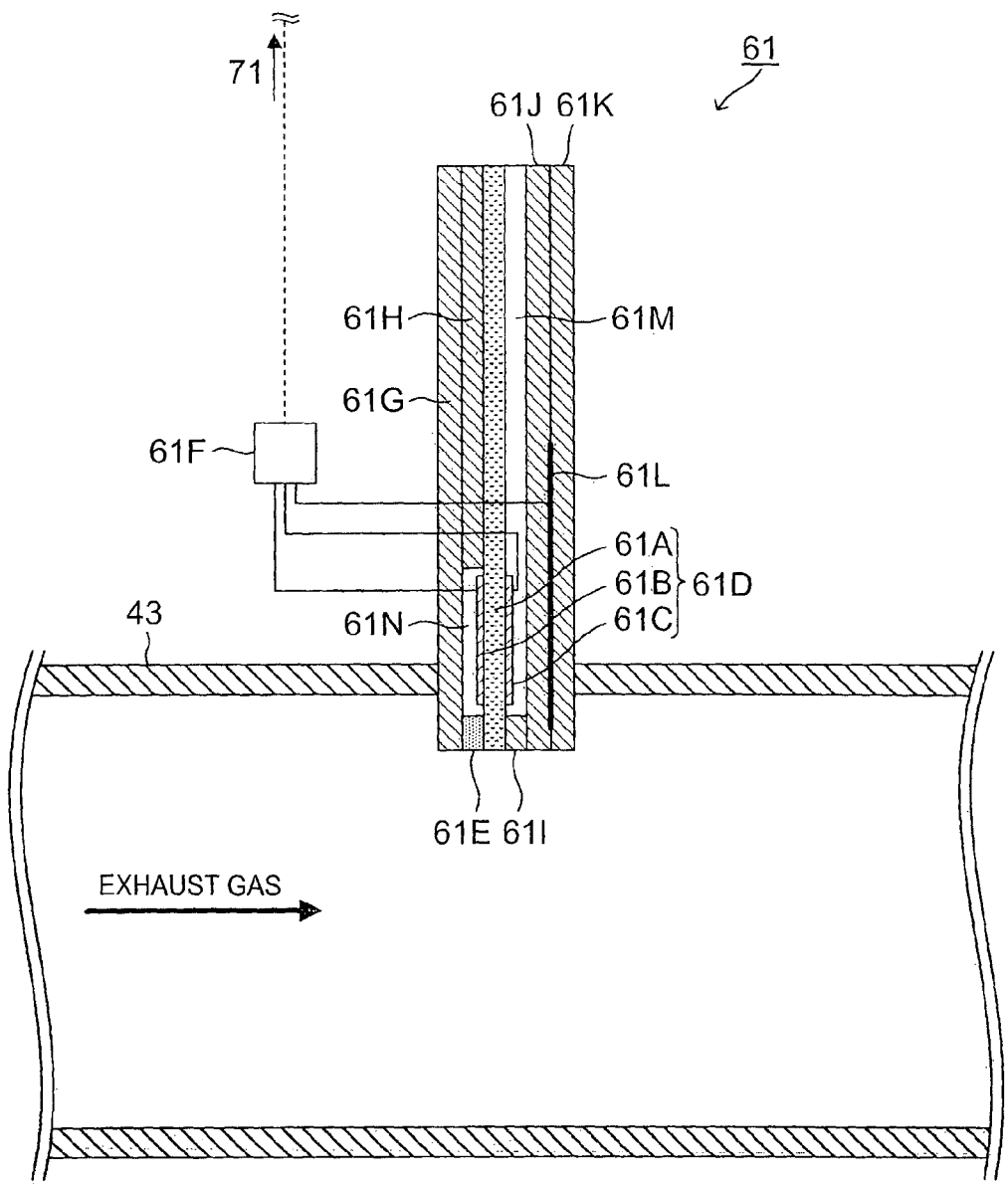
FIG. 2 is a schematic view that shows the schematic configuration of a limiting current oxygen concentration sensor (single-cell sensor) according to the embodiment.

As shown in FIG. 2, the limiting current oxygen concentration sensor 61 (hereinafter referred to as sensor 61) includes a sensor cell 61D, a diffusion-controlling layer 61E, a sensor control unit 61F, a first alumina layer 61G, a second alumina layer 61H, a third alumina layer 61I, a fourth alumina layer 61J, a fifth alumina layer 61K and a heater 61L. The sensor cell 61D is formed of a solid electrolyte layer 61A, a measuring electrode 61B and a reference electrode 61C. An atmosphere introduction passage 61M and an internal space 61N are formed in the sensor 61. The sensor 61 is a single-cell sensor having the single sensor cell 61D.

The sensor 61 is provided at the exhaust manifold 43 such that a distal end (a distal end at a side at which the diffusion-controlling layer 61E is provided) is exposed to exhaust gas. In consideration of the possibility that the concentration of SOx in exhaust gas changes by the exhaust gas purification catalyst 44, the sensor 61 is provided on the upstream side of the exhaust gas purification catalyst 44.

The solid electrolyte layer 61A is made of zirconia, or the like, that is able to conduct oxygen ions. The measuring electrode 61B and the reference electrode 61C are made of platinum group elements, such as platinum and rhodium, or an alloy including any one of the platinum group elements. The measuring electrode 61B and the reference electrode 61C are arranged so as to sandwich the solid electrolyte layer 61A. The measuring electrode 61B is arranged on one-side wall face of the solid electrolyte layer 61A (specifically, on an wall face that defines the internal space 61N). The reference electrode 61C is arranged on the other-side wall face of the solid electrolyte layer 61A (specifically, a wall face that defines the atmosphere introduction passage 61M).

The sensor control unit 61F is connected to the sensor cell 61D such that the measuring electrode 61B is a cathode and the reference electrode 61C is an anode. The sensor control unit 61F is connected to the heater 61L so as to be able to supply electric power to the heater 61L. The sensor control unit 61F is connected to the electronic control unit 71.

The sensor control unit 61F receives a command signal from the electronic control unit 71, applies the sensor cell 61D with a voltage corresponding to the command signal, and transmits the value of current that is output from the sensor cell 61D to the electronic control unit 71. The sensor control unit 61F receives a command signal from the electronic control unit 71, and supplies the heater 61L with an electric power corresponding to the command signal.

Application of a voltage to the sensor cell 61D is carried out by applying a voltage to the measuring electrode 61B and the reference electrode 61C so that a potential difference according to the command signal from the electronic control unit 71 is generated between the measuring electrode 61B and the reference electrode 61C (between an electrode pair).

The internal space 61N is a space defined by the solid electrolyte layer 61A, the diffusion-controlling layer 61E, the first alumina layer 61G and the second alumina layer 61H. The internal space 61N is separated by the diffusion-controlling layer 61E from a sensor outside (the inside of the exhaust manifold 43). The diffusion-controlling layer 61E has a porous structure. The diffusion-controlling layer 61E controls the rate of transfer of exhaust gas from the exhaust manifold 43 to the internal space 61N (by extension, diffusion of exhaust gas into the solid electrolyte layer 61A). The atmosphere introduction passage 61M is open to the atmosphere outside the sensor 61.

The sensor 61 is usually used to detect the concentration of oxygen in exhaust gas flowing inside the exhaust manifold 43. Specifically, when a voltage for measuring the concentration of oxygen (hereinafter, referred to as ordinary voltage) is applied to the sensor cell 61D, oxygen contained in exhaust gas inside the internal space 61N is ionized at the measuring electrode 61B. Oxygen ions pass from the measuring electrode 61B through the solid electrolyte layer 61A and migrate to the reference electrode 61C. Oxygen ions that have reached the reference electrode 61C return to oxygen through recombination, and the oxygen is released to the atmosphere introduction passage 61M. Migration of electrons due to the series of electrochemical reactions is measured by the sensor control unit 61F as an output current from the sensor cell 61D. Because of the function of the diffusion-controlling layer 61E, the magnitude of the output current (in other words, the amount of oxygen ions that migrate between the electrode pair) is in a one-to-one correspondence with the concentration of oxygen in exhaust gas. That is, the output current from the sensor cell 61D has a magnitude corresponding to the concentration of oxygen in exhaust gas. The output current is generally called limiting current.

Incidentally, the concentration of oxygen in exhaust gas mainly depends on the air-fuel ratio of air-fuel mixture before combustion. Conversely, the air-fuel ratio of air-fuel mixture can be estimated on the basis of the concentration of oxygen in exhaust gas. Therefore, the concentration of oxygen in exhaust gas is also referred to as the air-fuel ratio of exhaust gas. In accordance with such naming, for example, the concentration of oxygen in exhaust gas that is produced as a result of combustion of air-fuel mixture having a stoichiometric air-fuel ratio is substantially zero, and the air-fuel ratio of the exhaust gas is the stoichiometric air-fuel ratio. Hereinafter, an applied voltage to the sensor cell 61D is referred to as applied voltage to the sensor 61, and an output current from the sensor cell 61D is referred to as output current from the sensor 61.

Figure 3A:
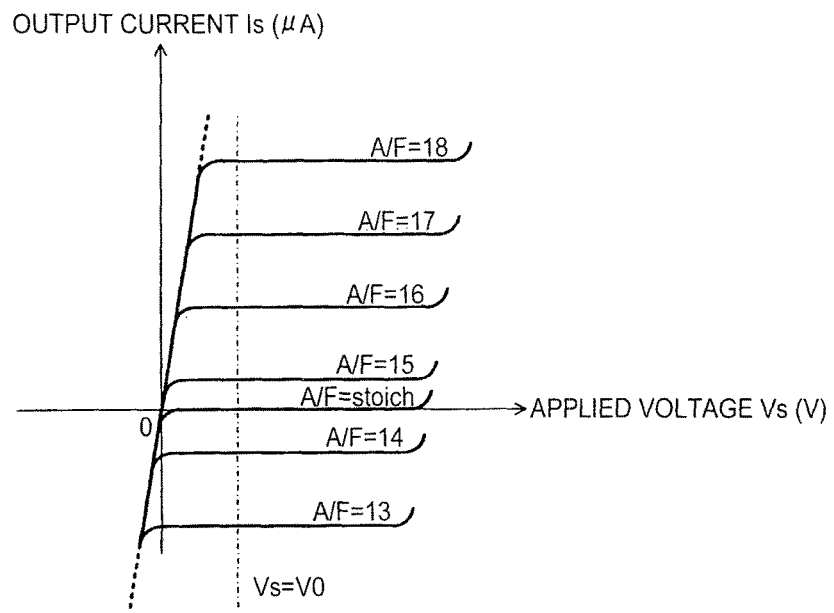
FIG. 3A and FIG. 3B are schematic graphs that show the output characteristics of the limiting current oxygen concentration sensor according to the embodiment.
Figure 3B:
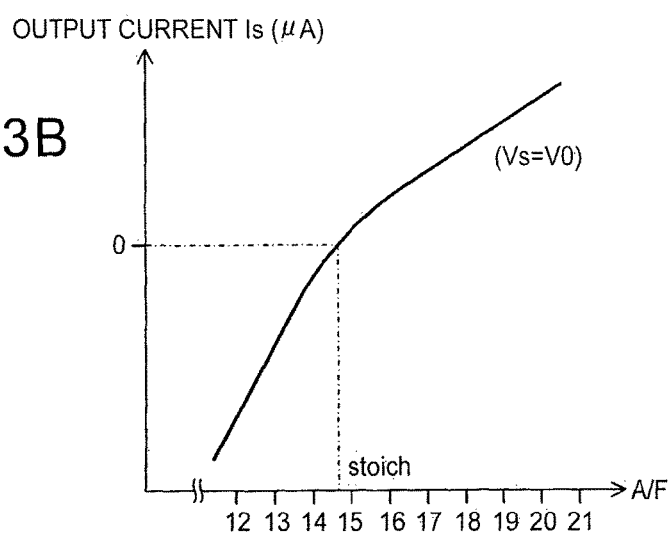

FIG. 3A is a schematic graph that shows the correlation among an air-fuel ratio A/F of exhaust gas, an applied voltage Vs to the sensor 61 and an output current Is from the sensor 61. As shown in the graph, the air-fuel ratio A/F of exhaust gas and the magnitude of output current Is (limiting current) have a one-to-one correspondence when the applied voltage Vs falls within a specific range. Therefore, a voltage that falls within the range is used as an ordinary voltage V0 (see the alternate long and short dashed line in the graph). The ordinary voltage V0 is a fixed value (for example, 0.4 V) that is generally determined on the basis of an experiment, or the like. FIG. 3B is a schematic graph that shows the correlation between an air-fuel ratio A/F of exhaust gas and an output current Is when the applied voltage Vs is the ordinary voltage V0. As shown in the graph, the air-fuel ratio A/F of exhaust gas is uniquely identified on the basis of the output current Is.

In the embodied system, the value of the output current Is of the sensor 61 is measured by the sensor control unit 61F, and is transmitted to the electronic control unit 71. The electronic control unit 71 identifies (detects) the air-fuel ratio A/F of exhaust gas by applying the received value of the output current Is of the sensor 61 to the correlation shown in FIG. 3B.

In this way, the sensor 61 provided in the engine 10 to which the embodied system is applied is a sensor having a characteristic of outputting a current (limiting current) that is in a one-to-one correspondence with the concentration of oxygen in exhaust gas. The sensor includes a solid electrolyte, the measuring electrode and the reference electrode (the electrode pair), and the diffusion-controlling layer. The solid electrolyte is able to conduct oxygen ions. The measuring electrode and the reference electrode are provided so as to sandwich the solid electrolyte. The diffusion-controlling layer is provided so as to cover the measuring electrode. In the sensor having the above configuration, an applied voltage to the sensor can translate to a voltage that is applied to the electrode pair in order to generate a potential difference between the electrode pair. An output current of the sensor can translate to a current that is output from the electrode pair.

Referring back to FIG. 1, the crank position sensor 65 is configured to output a signal indicating the rotation position of the crankshaft 28. The air flow meter 63 is configured to output a signal indicating the amount of air (intake air amount) per unit time, which is taken into the engine 10. The electronic control unit 71 calculates the amount of air that is introduced into the combustion chamber 23 on the basis of these signals. The accelerator operation amount sensor 64 outputs a signal indicating the opening degree of the accelerator pedal 51. On the basis of the signal, the electronic control unit 71 determines an output that is required of the engine 10.

The electronic control unit 71 is an electronic circuit mainly formed of a known microcomputer including a CPU, a ROM, a RAM, and the like. The CPU of the electronic control unit 71 is configured to transmit command signals to the fuel injection valve 21, the throttle valve 34, the sensor 61, and the like, and receive signals that are output from the plurality of sensors 61 to 64.

The embodied system detects the concentration of SOx in exhaust gas with the use of the sensor 61. A method of detecting the concentration of SOx in the embodied system will be described with reference to FIG. 4 to FIG. 7.

According to the experiment and consideration of the inventors, it has been found that, when the applied voltage Vs to the sensor 61 is gradually reduced from a specific first voltage V1 to a specific second voltage V2, the output current Is of the sensor 61 takes a unique extreme value corresponding to the concentration of SOx in exhaust gas. Hereinafter, the process of gradually reducing the applied voltage Vs to the sensor 61 from the first voltage V1 to the second voltage V2 is referred to as sweep process.

Figure 4:
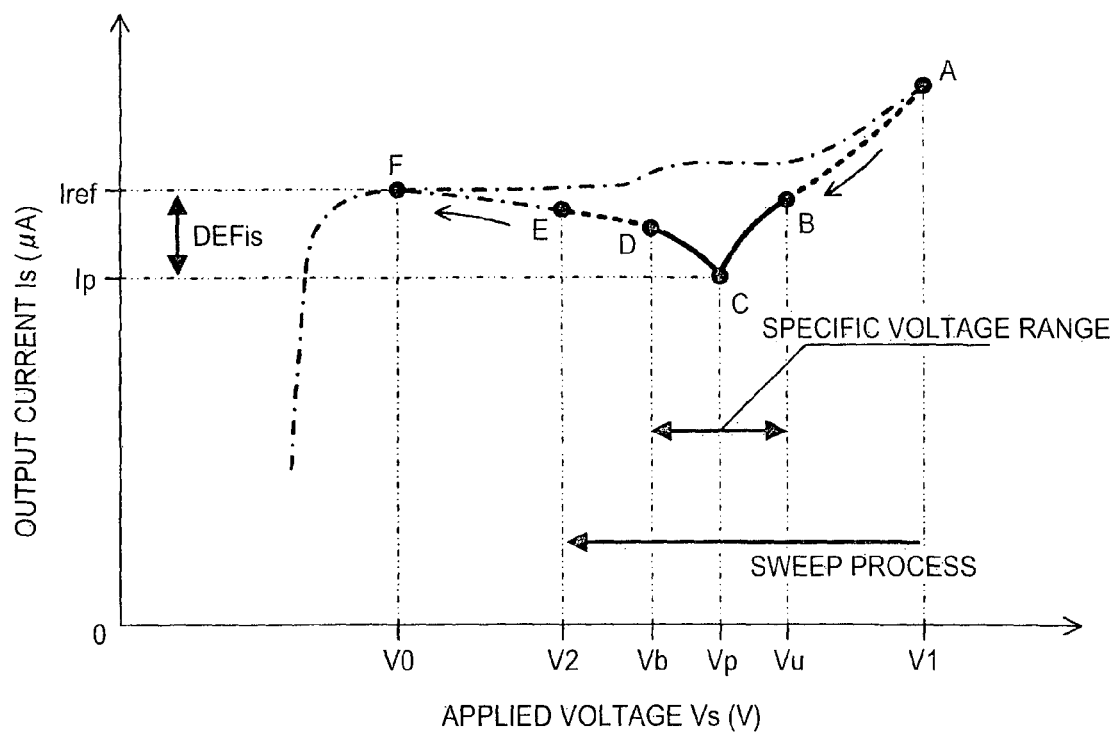
FIG. 4 is a schematic graph that shows an example of changes (waveform) in output current of the sensor when a sweep process is executed according to the embodiment.

Initially, the outline of the sweep process will be described. FIG. 4 is a schematic graph that shows an example of the waveform of the output current of the sensor 61 when the sweep process is executed. In the output current Is at the time when the applied voltage Vs decreases from the first voltage V1 to the second voltage V2 (in the graph, the waveform that connects point A, point B, point C, point D and point E), the local minimum (which is the output current at point C in the graph, and hereinafter referred to as peak value Ip) changes with the concentration of SOx in exhaust gas. However, the output current Is changes with not only the concentration of SOx in exhaust gas but also the air-fuel ratio (the concentration of oxygen) of exhaust gas during the sweep process. Therefore, the embodied system extracts a value indicating only the concentration of SOx in exhaust gas from the output current Is, and detects the concentration of SOx in exhaust gas on the basis of the extracted value. In order to accurately carry out the detection, the embodied system controls the engine 10 so that the air-fuel ratio of exhaust gas during the sweep process is kept at a constant value. The output current Is corresponding to the constant value is used as an output component (reference value Iref) corresponding to the air-fuel ratio of exhaust gas.

As shown in the graph, the first voltage V1 and the second voltage V2 are higher than the ordinary voltage V0 for measuring the concentration of oxygen. Thus, in the case where the concentration of oxygen is measured with the use of the sensor 61, when the sweep process is started, the embodied system changes the applied voltage Vs from the ordinary voltage V0 to the first voltage V1 (in the graph, see the waveform that connects point F and point A). When the sweep process has completed, the embodied system reduces the applied voltage Vs from the second voltage V2 to the ordinary voltage V0 (in the graph, see the waveform that connects point E and point F). In the example shown in the graph, for the sake of convenience, the embodied system keeps the air-fuel ratio of exhaust gas at a constant value not only during execution of the sweep process (a period from point A to point E) but also periods before and after the sweep process (a period from point F to point A and a period from point E to point F).

Specifically, when the sensor 61 is used to detect the air-fuel ratio of exhaust gas, the applied voltage Vs to the sensor 61 is the ordinary voltage V0 (see point F in the graph). When the embodied system executes the sweep process, the embodied system changes the applied voltage Vs from the ordinary voltage V0 to the first voltage V1 (see point A in the graph). Thus, SOx is reduced into sulfur in the sensor 61 (specifically, at the surface, or the like, of the measuring electrode 61B), and sulfur produced as a result of the reduction is accumulated in the sensor 61 (the surface, or the like, of the measuring electrode 61B). The amount of sulfur that is accumulated in the sensor 61 corresponds to the concentration of SOx in exhaust gas.

This is because sulfur (S) is a solid at a temperature at which the sensor 61 is usually used and sulfur (S) accumulates in the sensor 61 without volatizing from the sensor 61. In addition, this is because, as well as the fact that the value of limiting current in the sensor 61 increases as the concentration of oxygen in exhaust gas increases, the amount of SOx that is accumulated per unit time in the sensor 61 increases as the concentration of SOx in exhaust gas increases.

Because the first voltage V1 is higher than the ordinary voltage V0, when the applied voltage Vs is the first voltage V1, oxygen in exhaust gas is also ionized in the sensor 61, and a component other than SOx (for example, $H_2O$) in exhaust gas can also be decomposed in the sensor 61. However, oxygen ions are emitted from the sensor 61 in accordance with the oxygen measuring principle (see the above description) of the sensor 61, and a substance (for example, $H_2$) that is produced as a result of decomposition of a component other than SOx is generally gas at the above-described temperature, so the substance is not accumulated in the sensor 61. Thus, when the applied voltage Vs is the first voltage V1, only sulfur is substantially accumulated in the sensor 61.

In this way, the first voltage V1 is an applied voltage at which sulfur that is produced as a result of reduction of SOx into sulfur in the sensor 61 is accumulated in the sensor 61. In this example, the first voltage V1 is a voltage (for example, 1.0 V) that is confirmed by an experiment, or the like, in advance that the reduction and accumulation occur, and is recorded in the ROM of the electronic control unit 71.

When the applied voltage Vs is changed from the ordinary voltage V0 to the first voltage V1, the output current Is of the sensor 61 increases (see point A in the graph) as shown in the graph because of the above-described reduction, and the like, of SOx.

Subsequently, the embodied system executes the sweep process while controlling the engine 10 so that the air-fuel ratio of exhaust gas is kept at a constant value. Thus, the embodied system gradually reduces the applied voltage Vs from the first voltage V1. During execution of the sweep process, oxidation of sulfur into SOx, decomposition of oxygen and decomposition of another component in exhaust gas occur in the sensor 61. Therefore, an output component due to each of those reactions is included in the output current Is. However, according to the experiment, and the like, of the inventors, the output component due to the other component is smaller than the output component due to SOx and oxygen, and it may be ignored from the viewpoint of detecting the concentration of SOx. Thus, the output component Is during execution of the sweep process substantially includes the output component due to sulfur (specifically, SOx) and the output component due to oxygen.

Therefore, if the concentration of oxygen in exhaust gas excessively fluctuates during execution of the sweep process, the output current Is may significantly change so as to reflect the fluctuations in the concentration of oxygen, and the accuracy of measuring the output component due to sulfur (specifically, SOx) may decrease. Therefore, the embodied system executes the sweep process while keeping the air-fuel ratio of exhaust gas at a constant value. Thus, because the output component due to oxygen, included in the output current Is, is kept constant (kept at the value of limiting current corresponding to the concentration of oxygen having the constant value), the output current Is does not fluctuate because of fluctuations in the concentration of oxygen.

As a result, the output current Is draws the waveform having the unique peak value Ip corresponding to the concentration of SOx in exhaust gas. Specifically, the output current Is draws the waveform that once decreases and increases again after passing through the peak value Ip with a decrease in applied voltage Vs (see the waveform from point A to point E in the graph).

Incidentally, according to the experiment, and the like, of the inventors, it has been found that the applied voltage at the time when the output current Is reaches the peak value Ip (hereinafter, referred to as peak output voltage Vp) changes with the concentration of oxygen (air-fuel ratio A/F) in exhaust gas during execution of the sweep process.

Figure 5:
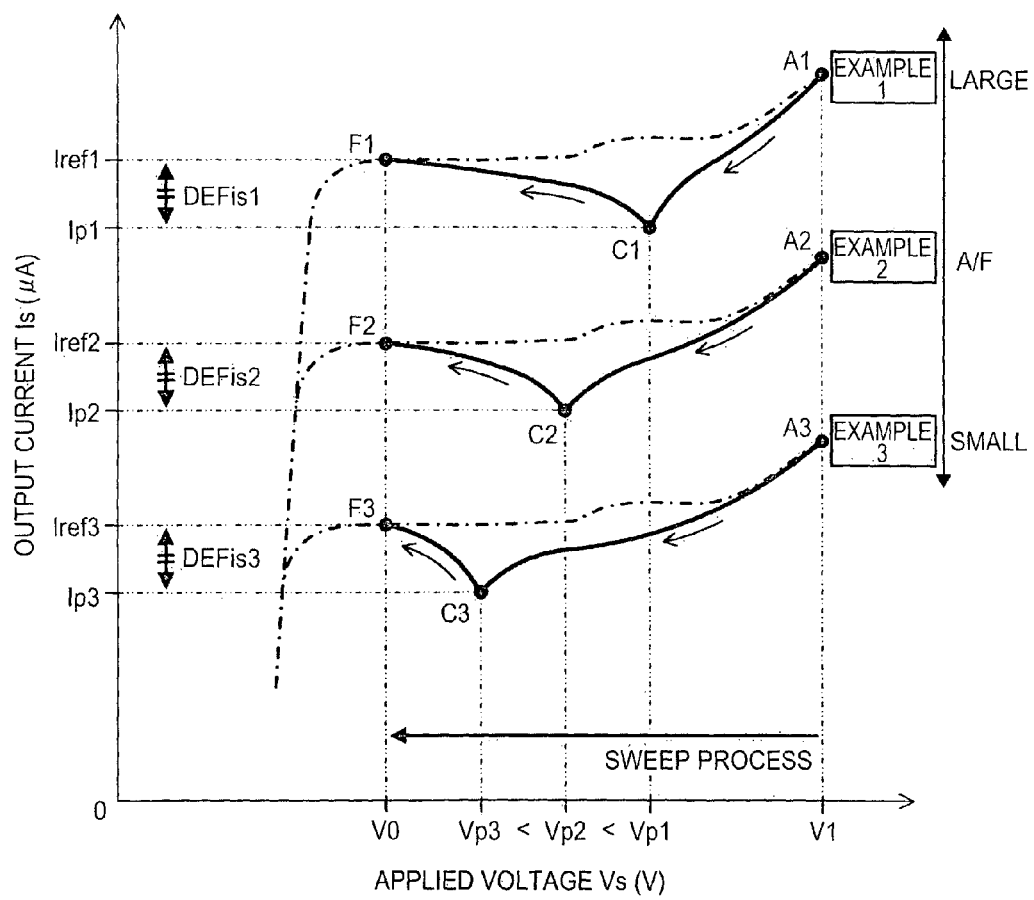
FIG. 5 is a schematic graph that shows the correlation between an air-fuel ratio (a concentration of oxygen) in exhaust gas during the sweep process and a peak output voltage according to the embodiment.

As a specific example, FIG. 5 shows the waveforms of the output currents Is of three examples in which the air-fuel ratio A/F of exhaust gas during the sweep process is different (however, the concentration of SOx in exhaust gas is the same in each example). For the sake of convenience, in the illustrated three examples, the sweep process is continued from the first voltage V1 to the ordinary voltage V0.

As shown in the graph, the air-fuel ratio A/F of exhaust gas during the sweep process decreases in order of Example 1, Example 2 and Example 3. As shown in the waveform of Example 1 (the continuous line that connects. A1, C1 and F1 in the graph), a peak output voltage in Example 1 is Vp1. As shown in the waveform of Example 2 (the continuous line that connects A2, C2 and F2 in the graph), a peak output voltage in Example 2 is a value Vp2 lower than the value Vp1. In addition, as shown in the waveform of Example 3 (the continuous line that connects A3, C3 and F3 in the graph), a peak output voltage in Example 3 is a value Vp3 lower than the value Vp2. That is, as the air-fuel ratio A/F of exhaust gas during the sweep process decreases, the peak output voltage Vp decreases.

Figure 6:
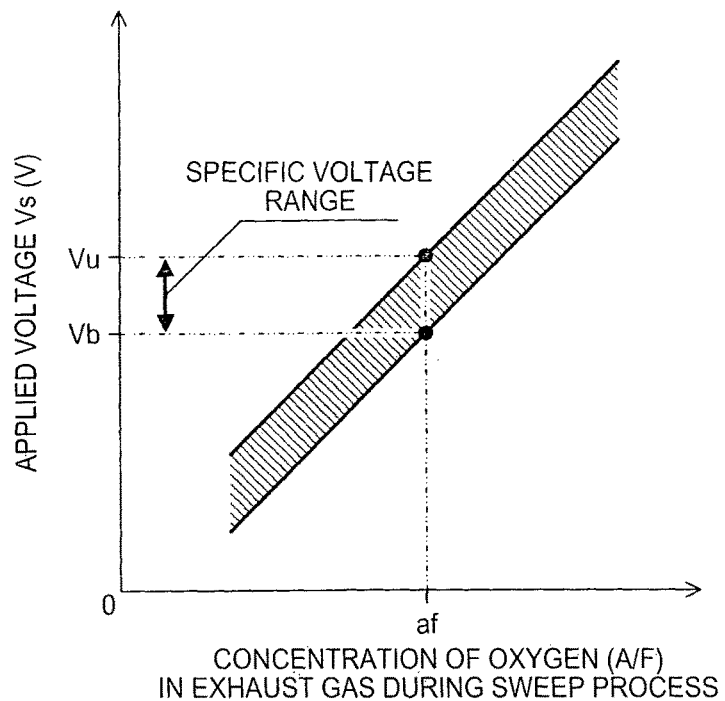
FIG. 6 is a schematic graph that shows the correlation between an air-fuel ratio (a concentration of oxygen) in exhaust gas during the sweep process and a specific voltage range according to the embodiment.

Under an ideal condition in which there is no influence, such as disturbance, the air-fuel ratio A/F of exhaust gas during the sweep process is in a one-to-one correspondence with the peak output voltage Vp. However, actually, due to the influence of various disturbances, and the like, even when the air-fuel ratio A/F of exhaust gas during the sweep process is the same, slight variations may occur in the peak output voltage Vp. Therefore, as shown in FIG. 6, the embodied system determines the range of the applied voltage Vs in which the peak value Ip is predicted to be output (the range in which the peak output voltage Vp is predicted to be included, and hereinafter referred to as specific voltage range) on the basis of the air-fuel ratio A/F of exhaust gas during the sweep process. For example, when the air-fuel ratio A/F of exhaust gas is a value af, the specific voltage range is determined to a range from an upper limit value Vu to a lower limit value Vb. The correlation shown in FIG. 6 is determined by an experiment, or the like, in advance, and is recorded in the ROM of the electronic control unit 71.

Referring back to FIG. 4, when the embodied system starts the sweep process, the embodied system determines the specific voltage range on the basis of the air-fuel ratio A/F (constant value) of exhaust gas. In this example, it is assumed that the air-fuel ratio A/F is the value af and the specific voltage range is determined to the range from the upper limit value Vu to the lower limit value Vb (Vb≤Vs≤Vu).

The embodied system acquires (measures) the peak value Ip from the output current Is in the specific voltage range (see the continuous line that connects point B, point C and point D in the graph). The embodied system completes the sweep process (see point E in the graph) at predetermined timing after the peak value Ip is output. The applied voltage Vs at the timing at which the sweep process is completed is the second voltage V2. In this way, the second voltage V2 is an applied voltage for obtaining the unique peak value Ip corresponding to the concentration of SOx in exhaust gas, and is an applied voltage at which sulfur is oxidized (reoxidized) into SOx in the sensor 61.

After that, the embodied system returns the applied voltage Vs to the ordinary voltage V0 (see point F in the graph). As described above, in the example shown in the graph, the embodied system keeps the air-fuel ratio of exhaust gas at the same constant value (the value af in this example) as the air-fuel ratio during the sweep process until the applied voltage Vs is returned to the ordinary voltage V0. Therefore, the embodied system uses, as the reference value Iref, the output current Is at the time when the applied voltage Vs is returned to the ordinary voltage V0.

The embodied system detects the concentration of SOx in exhaust gas on the basis of the reference value Iref and the peak value Ip of the output current Is obtained during the sweep process. Thus, the embodied system is able to analyze the output component due to the concentration of SOx in exhaust gas as distinguished from the output component due to another component.

As an example of the detection, as shown in the graph, the embodied system identifies (detects) the concentration of SOx in exhaust gas on the basis of the absolute value DEFis of a difference between the peak value Ip and the reference value Iref. Specifically, according to the experiment, and the like, of the inventors, as shown in FIG. 7, the concentration Csox of SOx increases as the absolute value DEFis of the difference increases.

Figure 7:
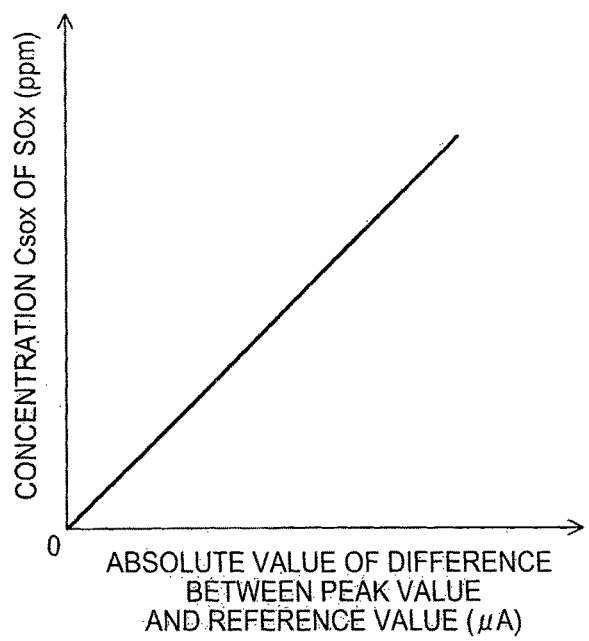
FIG. 7 is a schematic graph that shows the correlation between a concentration of SOx in exhaust gas and an output of the sensor according to the embodiment.

Therefore, the embodied system calculates the absolute value DEFis of the above-described difference from the peak value Ip and the reference value Iref, and applies the absolute value DEFis of the difference to the correlation shown in FIG. 7. Thus, the embodied system identifies (detects) the concentration Csox of SOx in exhaust gas. The correlation shown in FIG. 7 is determined by an experiment, or the like, in advance, and is recorded in the ROM of the electronic control unit 71.

As described above, the reference value Iref is used to extract only the output component due to the concentration of SOx from the output current Is. Therefore, the reference value Iref can, for example, translate to the output current of the sensor at the time when the engine is controlled so that the concentration of oxygen in exhaust gas is the constant value in the case where the output current of the sensor depends on only the concentration of oxygen in exhaust gas.

As shown in FIG. 5, even when the air-fuel ratio A/F of exhaust gas during the sweep process is different, but when the concentration of SOx is the same, the absolute value DEFis of the above-described difference is the same (in the graph, a value DEFis1, a value DEFis2 and a value DEFis3 are equal to one another). That is, irrespective of the air-fuel ratio A/F of exhaust gas during the sweep process, the correlation shown in FIG. 7 may be used.

In addition, in FIG. 6, irrespective of the value of the air-fuel ratio A/F during the sweep process, the width of the specific voltage range (the difference between the upper limit value Vu and the lower limit value Vb) is set to a constant value. However, the width of the specific voltage range may be set to vary with the value of the air-fuel ratio A/F during the sweep process.

The principle of occurrence of the peak value Ip of output current during execution of the sweep process and the principle of a change in the peak output voltage Vp with the air-fuel ratio (the concentration of oxygen) during execution of the sweep process are not apparent at this point in time. However, in cyclic voltammetry that is a general method of measuring the electrochemical property of a physical object, it is known that the peak of response current occurs near an oxidation-reduction potential because of a rate-controlling phenomenon of electrons or oxides. A phenomenon similar to this phenomenon is presumed to be occurring during the sweep process of the invention.

An example of detection at the time when the above-described detection method is actually applied to the engine 10 will be described with reference to FIG. 8 and FIG. 9. In this example, the embodied system executes the sweep process during a specific period (between time t1 and time t2) after the timing at which a condition (described later in detail) for detecting the concentration of SOx in exhaust gas is satisfied, and detects the concentration of SOx in exhaust gas.

Figure 8:
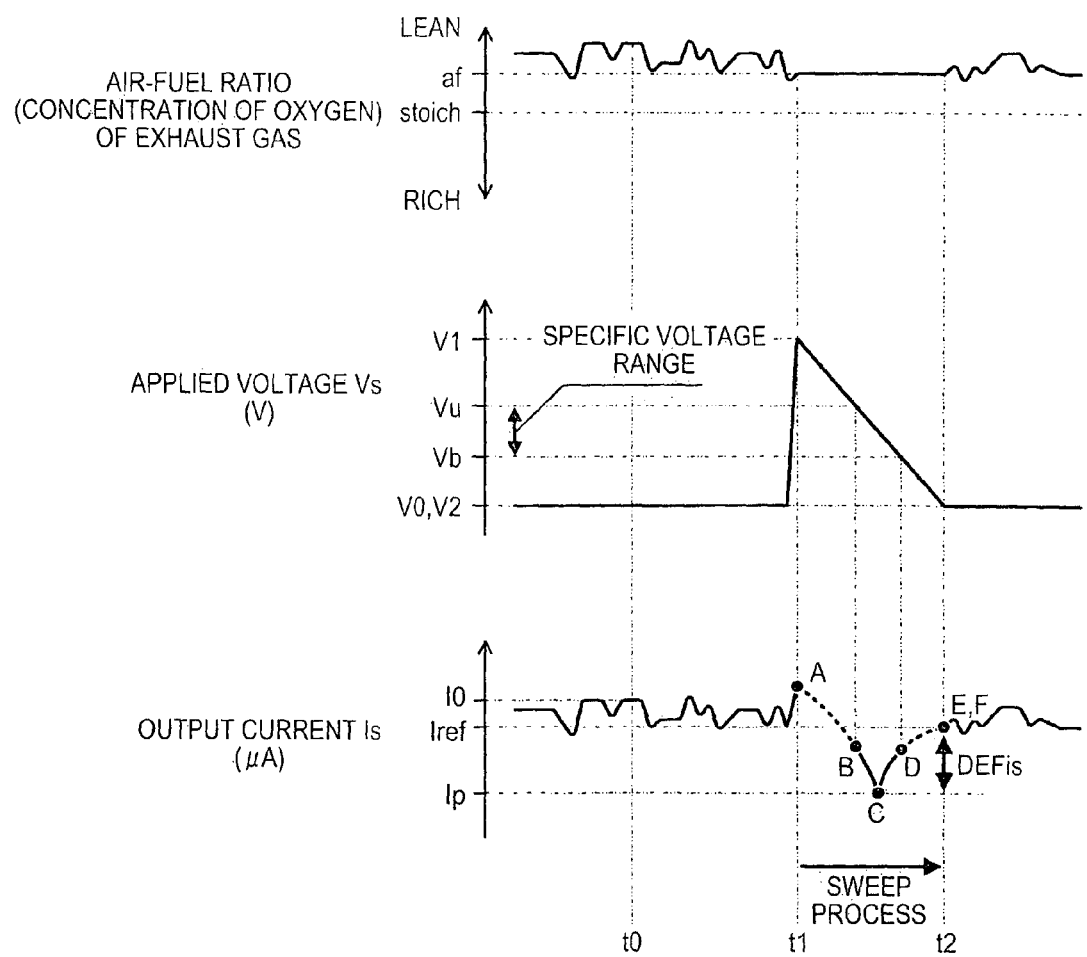
FIG. 8 is a time chart that shows an example of the correlation among an air-fuel ratio (a concentration of oxygen) in exhaust gas, an applied voltage to the sensor and an output current of the sensor according to the embodiment.
Figure 9:
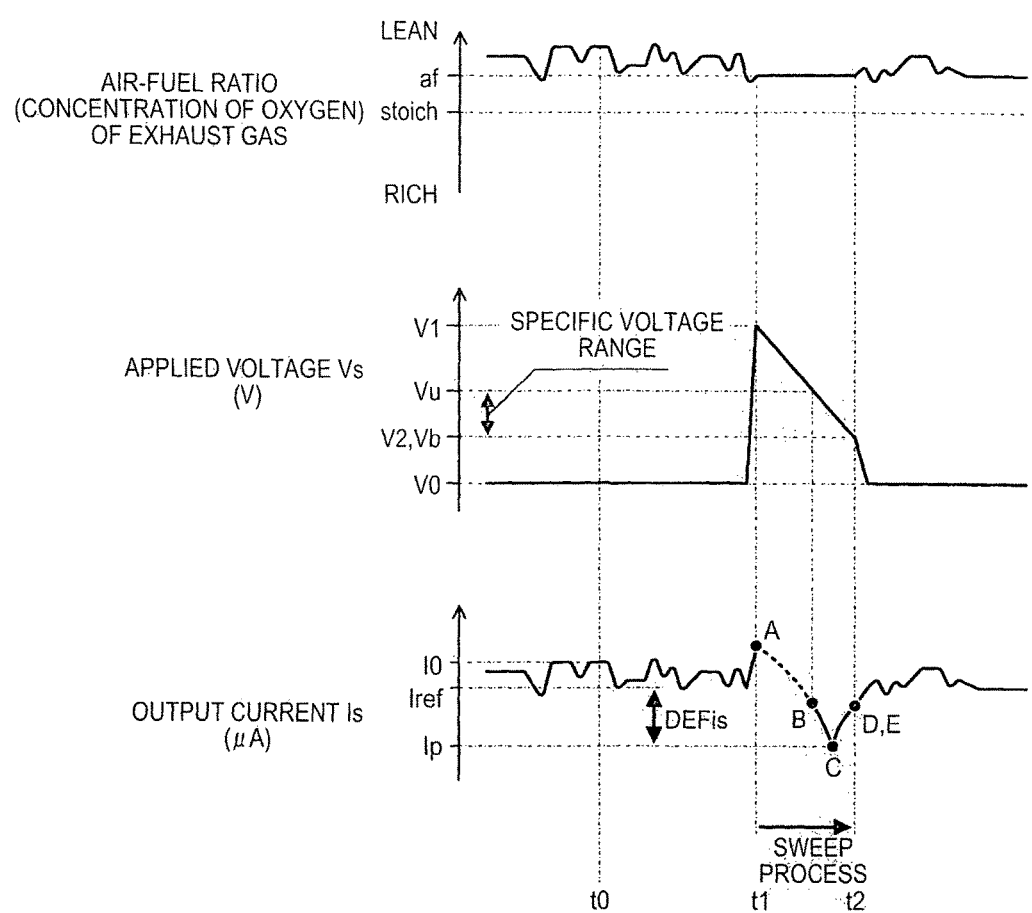
FIG. 9 is a time chart that shows another example of the correlation among an air-fuel ratio (a concentration of oxygen) in exhaust gas, an applied voltage to the sensor and an output current of the sensor according to the embodiment.

Specifically, at time t0 in FIG. 8, the air-fuel ratio of exhaust gas changes on the basis of a required output, or the like, of the engine 10 irrespective of the detected concentration of SOx. At time t0, in order to measure the air-fuel ratio of exhaust gas with the use of the sensor 61, the applied voltage Vs to the sensor 61 is set to the ordinary voltage V0. The output current Is of the sensor 61 at time t0 is a value I0 corresponding to the air-fuel ratio of exhaust gas.

After that, at the predetermined timing, the embodied system increases the applied voltage Vs from the ordinary voltage V0 to the first voltage V1 in order to start the sweep process. At time t1 in the graph, the applied voltage Vs reaches the first voltage V1 (see point A in the graph). In this example, the embodied system executes the sweep process while keeping the air-fuel ratio af of exhaust gas at time t1. That is, the embodied system controls the engine 10 so that the air-fuel ratio of exhaust gas during execution of the sweep process is kept at the constant value af (for example, the operating state of the engine 10 at time t1 is kept as it is). Point A, point B, point C, point D, point E and point F in the graph respectively correspond to point A, point B, point C, point D, point E and point F in FIG. 4. However, different from the example shown in FIG. 4, in this example, the air-fuel ratio at timing other than during execution of the sweep process is not specifically controlled to a constant value.

The embodied system executes the sweep process during the period from time t1 to time t2. Specifically, the embodied system gradually reduces the applied voltage Vs from the first voltage V1 to the second voltage V2 at a constant rate while keeping the air-fuel ratio of exhaust gas at the constant value af. In this example, the second voltage V2 is set to the same voltage as the ordinary voltage V0. In addition, the embodied system determines the specific voltage range (Vb≤Vs≤Vu) by applying the constant value af to a map that expresses the correlation between an air-fuel ratio and a specific voltage range (which is recorded in the ROM of the electronic control unit 71, and see FIG. 6). The embodied system records the output currents Is while the applied voltage Vs included in the specific voltage range is applied to the sensor 61 during the sweep process (the continuous line that connects point B, point C and point D in the graph) in the RAM of the electronic control unit 71.

The embodied system calculates the peak value Ip (see point C in the graph) on the basis of the output currents Is recorded in the RAM. In addition, the embodied system uses the output current Is at time t2 as the reference value Iref (see point E and point F in the graph). At time t2, the sweep process completes. Subsequently, the embodied system calculates the absolute value DEFis of the difference between the peak value Ip and the reference value Iref. The embodied system detects the concentration Csox of SOx in exhaust gas by applying the absolute value DEFis of the difference to a map that expresses the correlation between the absolute value DEFis of the difference and the concentration of SOx in exhaust gas (the correlation shown in FIG. 7 is recorded in the ROM of the electronic control unit 71).

After the sweep process completes (after time t2), the applied voltage Vs is kept at the ordinary voltage V0, and the air-fuel ratio of exhaust gas is detected again. After time t2, the air-fuel ratio of exhaust gas changes on the basis of the required output, and the like, of the engine 10 again.

After the embodied system calculates the absolute value DEFis of the above-described difference, the embodied system may use the absolute value DEFis of the difference itself in a process (for example, an alarm for informing a high concentration of SOx or measurement of the concentration of sulfur in fuel) as a value that is in a one-to-one correspondence with the concentration of SOx without obtaining the concentration Csox of SOx.

The embodied system does not necessarily need to detect the concentration of SOx as shown in FIG. 8. For example, as shown in FIG. 9, the embodied system can set the second voltage V2 to an applied voltage that does not coincide with the ordinary voltage V0. The second voltage V2 is the applied voltage Vs at which the sweep process is completed. Specifically, in this example, the embodied system momentarily monitors the output current Is that is recorded in the RAM while the applied voltage Vs included in the specific voltage range is applied to the sensor 61 during the sweep process. The embodied system completes the sweep process at any timing after the output of the peak value Ip has been confirmed. The applied voltage Vs at the time when the embodied system completes the sweep process in this way is the second voltage V2 (see point D and point E in FIG. 9). In this example, the second voltage V2 and the lower limit value Vb of the specific voltage range are set to the same voltage; however, the second voltage V2 and the lower limit value Vb do not necessarily need to be the same.

In this example, there is a possibility that the output current Is at time t2 at which the sweep process completes includes not only the output component due to the air-fuel ratio of exhaust gas but also the output component due to the concentration of SOx. Therefore, the output current Is at the completion (time t2 in FIG. 8) of the sweep process cannot be used as the reference value Iref unlike the example of detection shown in FIG. 8. Therefore, in this example, an output current during the sweep process, measured by another oxygen concentration sensor (not shown) different from the sensor 61, or an output current that is obtained by applying the air-fuel ratio of exhaust gas, estimated from the operating state of the engine 10 during the sweep process, to the map shown in FIG. 3B is used as the reference value Iref. When another sensor is used, in order to increase the detection accuracy of the concentration of SOx, it is desirable that the output characteristic of the other sensor and the output characteristic of the sensor 61 be the same or the output current of the other sensor be converted (corrected) to the output current of the sensor 61 and used.

In this example of detection, the process of detecting the concentration of SOx can be complicated as compared to the example of detection shown in FIG. 8. However, this example of detection is advantageous in that the length of time during which the sweep process is executed is shortened as compared to the example of detection shown in FIG. 8.

In addition, the embodied system can use an air-fuel ratio other than the air-fuel ratio of of exhaust gas at the start (time t1) of the sweep process as the air-fuel ratio (the concentration of oxygen) in exhaust gas during the sweep process. For example, a preset single fixed value, a value selected from among a plurality of prepared fixed values, or the like, can be used as the air-fuel ratio of exhaust gas during the sweep process.

As described above, the waveform of the output current Is during the sweep process occurs as a result of reoxidation of sulfur accumulated in the sensor 61. Therefore, the concentration of SOx in exhaust gas, which is detected by the embodied system, strictly indicates the concentration of SOx in exhaust gas at the timing at which sulfur is accumulated in the sensor 61 (at the start of the sweep process). On the other hand, depending on the configuration, arrangement, and the like, of the sensor 61, a certain length of time may be required in order to sufficiently accumulate sulfur having a sufficient amount for detecting the concentration of SOx. In this case, the concentration of SOx, which is detected by the embodied system, indicates the average value of the concentration of SOx in exhaust gas during a period during which sulfur is accumulated in the sensor 61.

An actual operation of the embodied system will be described with reference to FIG. 10. In the embodied system, the CPU of the electronic control unit 71 executes a routine shown in FIG. 10, executes the sweep process while controlling the engine 10 so that the air-fuel ratio (the concentration of oxygen) of exhaust gas is kept at a constant value, and detects the concentration of SOx in exhaust gas on the basis of the output current Is in the specific voltage range.

Figure 10:
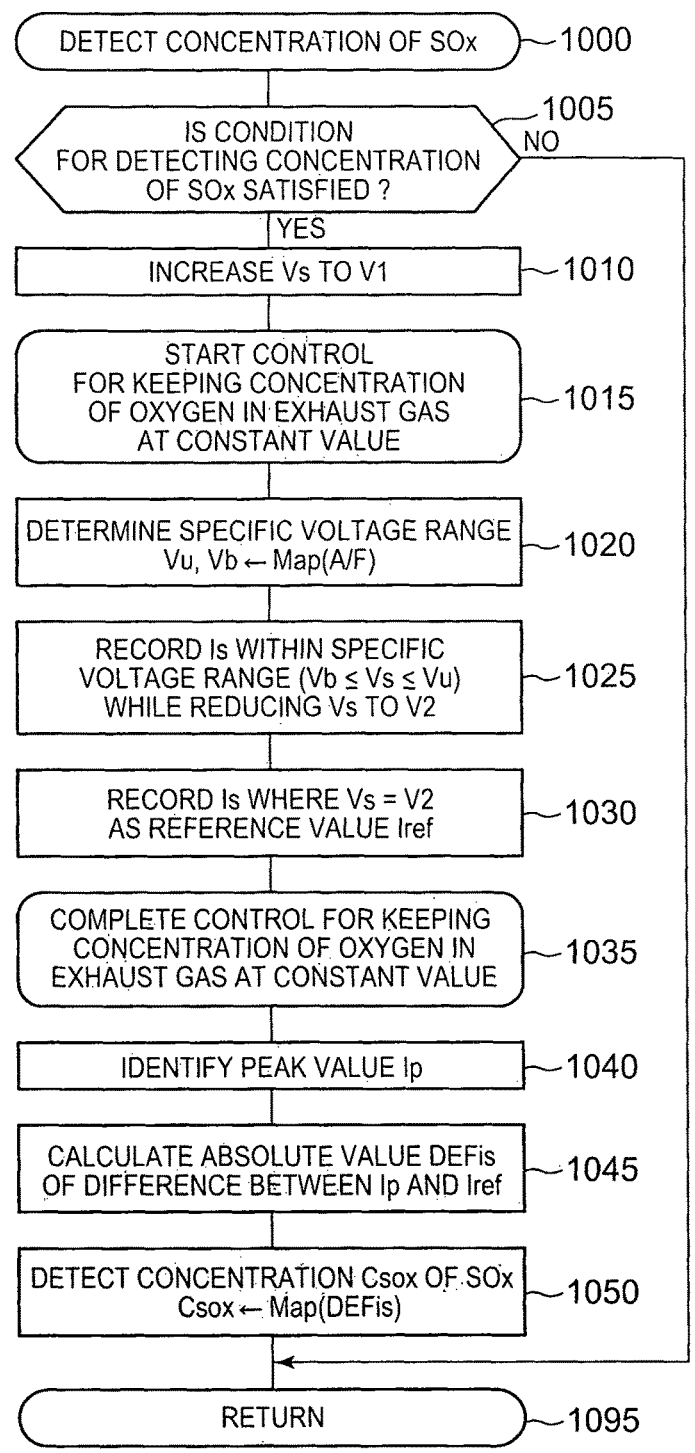
FIG. 10 is a flowchart that shows a routine that is executed by a control system according to the embodiment.

Specifically, the CPU executes the routine of detecting the concentration of SOx in FIG. 10 each time a predetermined time elapses. When the process of the routine is started, the CPU proceeds to step 1005, and determines whether the condition for detecting the concentration of SOx is satisfied at present timing. In this example, the condition is satisfied when the engine 10 is operated in a steady state and the concentration of SOx has not been detected once from when a vehicle on which the engine 10 is mounted is refueled last time to the present timing.

When the above condition is satisfied, the CPU makes affirmative determination in step 1005, and proceeds to step 1010. In this step, the CPU transmits, to the sensor 61 (to the sensor control unit 61F), a command signal for increasing the applied voltage Vs to the sensor 61 to the first voltage V1. In accordance with the command signal, the sensor 61 increases the applied voltage Vs to the first voltage V1. Before transmitting the command signal, the CPU transmits, to the sensor 61, a command signal for keeping the applied voltage Vs at the ordinary voltage V0.

Subsequently, the CPU proceeds to step 1015. In this step, the CPU starts control for keeping the concentration of oxygen in exhaust gas at a constant value. In this example, the CPU keeps the air-fuel ratio of exhaust gas by, while considering the intake air amount, adjusting a fuel injection amount so that the air-fuel ratio (the concentration of oxygen) of exhaust gas is kept at the present timing (the start timing of the sweep process). Thus, the constant value in this example is the value of the concentration of oxygen in exhaust gas at the timing at which the sweep process is started. Because the concentration of oxygen in exhaust gas (air-fuel ratio) is stabilized through this control, this control is also referred to as stabilizing control.

Subsequently, the CPU proceeds to step 1020. In this step, the CPU determines the specific voltage range (the upper limit value Vu and lower limit value Vb of the range) by applying the air-fuel ratio at the time when the sweep process is executed (that is, the concentration of oxygen having a constant value, and, in this example, the concentration of oxygen at the start timing of the sweep process) to a lookup table (Map(A/F) in FIG. 6) that expresses the correlation between an air-fuel ratio A/F of exhaust gas and a specific voltage range. The specific voltage range is substantially determined simultaneously with the start of the sweep process.

Subsequently, the CPU proceeds to step 1025. In this step, while the CPU transmits, to the sensor 61, a command signal for gradually reducing the applied voltage Vs from the first voltage V1 to the second voltage V2, the CPU records, in the RAM, only the output currents Is at the time when the applied voltage Vs is included in the specific voltage range from among the output currents Is received from the sensor 61. In this example, the second voltage V2 is set to the same voltage as the ordinary voltage V0.

Subsequently, the CPU proceeds to step 1030. In this step, the CPU records, in the RAM, the output current Is at the timing at which the applied voltage Vs has reached the second voltage V2 (=ordinary voltage V0) as the reference value Iref. After that, the CPU proceeds to step 1035, and completes stabilizing control.

Subsequently, the CPU proceeds to step 1040. In this step, the CPU calculates the peak value Ip of the output current Is on the basis of the output currents Is recorded in the RAM within the specific voltage range during the sweep process. For example, the CPU calculates the rate of change in the output current Is at intervals of a predetermined time, and calculates the output current Is at the timing at which the rate of change is zero (the timing at which the rate of change is inverted from a positive value to a negative value) as the peak value Ip. Alternatively, for example, the CPU may calculate a minimum value among the output currents Is (sample values) recorded in the RAM as the peak value Ip.

The series of processes in step 1025 to step 1040 can be, for example, replaced with the following process.

(Process 1) All the output currents Is during the sweep process are stored in the RAM, and then the peak value Ip is calculated on the basis of only the output currents Is at the time when the applied voltage Vs is included in the specific voltage range from among the stored output currents Is.
(Process 2) Only the output currents Is at the time when the applied voltage Vs is included in the specific voltage range are received and stored in the RAM (that is, when the applied voltage Vs is not included in the specific voltage range, reception of the output current Is is prohibited), and then the peak value Ip is calculated on the basis of the stored output currents Is.
(Process 3) The output current Is at the timing at which the applied voltage Vs coincides with the upper limit value Vu of the specific voltage range is stored in the RAM as the peak value Ip, after that, the peak value Ip is compared with the output current Is each time the output current is sampled, and, when the output current Is is smaller than the peak value Ip, the output current Is is employed (updated) as a new peak value Ip. These steps are repeated until the applied voltage Vs coincides with the lower limit value Vb of the specific voltage range.

Subsequently, the CPU proceeds to step 1045. In this step, the CPU calculates the absolute value DEFis of the difference between the peak value Ip and the reference value Iref. The CPU proceeds to step 1050. In this step, the CPU identifies the concentration Csox of SOx by applying the calculated absolute value DEFis of the difference to a lookup table (Map(DEFis) in the flowchart) that expresses the correlation between the concentration Csox of SOx and the absolute value DEFis of the above-described difference. That is, in step 1050, the concentration Csox of SOx is detected.

After that, the CPU proceeds to step 1095, and once ends the routine. When the condition for detecting the concentration of SOx is not satisfied at the time when step S1005 of the routine is executed, the CPU makes negative determination in step 1005, directly proceeds to step 1095, and ends the routine.

In this way, the embodied system executes the sweep process while controlling the engine 10 so that the concentration of oxygen in exhaust gas (air-fuel ratio) is kept at a constant value, and identifies (detects) the concentration Csox of SOx in exhaust gas on the basis of the reference value Iref and the output currents Is of the sensor 61 within the specific voltage range during the sweep process. Thus, the embodied system is able to accurately detect the concentration Csox of SOx in exhaust gas by preventing erroneous measurement of the peak value Ip due to unintended noise, and the like, as much as possible while excluding the influence of components other than SOx in exhaust gas (for example, oxygen and $H_2O$) as much as possible.

The invention is not limited to the above-described embodiment. Various alternative embodiments may be employed within the scope of the invention. For example, the sensor 61 included in the engine 10 to which the embodied system is applied is a single-cell sensor having the single sensor cell 61D. Instead, the engine 10 may include a sensor having a plurality of the sensor cells 61D (for example, dual-cell sensor) instead of the sensor 61.

FIG. 11 is a schematic view that shows the schematic configuration of the dual-cell sensor. As shown in the drawing, the dual-cell sensor 62 includes a sensor cell 62D1 and a sensor cell 62D2. The sensor cell 62D1 includes a solid electrolyte layer 62A1, a measuring electrode 62B1 and a reference electrode 62C1. The sensor cell 62D2 includes a solid electrolyte layer 62A2, a measuring electrode 62B2 and a reference electrode 62C2. The sensor cell 62D1 is also referred to as upstream-side cell. The sensor cell 62D2 is also referred to as downstream-side cell.

The dual-cell sensor 62 further includes a diffusion-controlling layer 62E, a sensor control unit 62F, a first alumina layer 62G, a second alumina layer 62H, a third alumina layer 62I, a fourth alumina layer 62J, a fifth alumina layer 62K, a sixth alumina layer 62L and a heater 62M. In addition, an atmosphere introduction passage 62N and an internal space 62O are formed in the dual-cell sensor 62. The dual-cell sensor 62, as well as the sensor 61 (see FIG. 2), just needs to be provided at the exhaust manifold 43.

After the dual-cell sensor 62 discharges oxygen in exhaust gas to the outside of the internal space 61N with the use of the upstream-side cell 62D1, the dual-cell sensor 62 is able to detect the concentration of SOx in exhaust gas with the use of the downstream-side cell 62D2. Thus, when the concentration of SOx is detected by the dual-cell sensor 62, the output component due to oxygen is not substantially included in the output current of the downstream-side cell 62D2. Therefore, in comparison with the case where the single-cell sensor is used (in the case of the embodied system), the influence of a change in the concentration of oxygen in exhaust gas on detection of the concentration of SOx is small. However, even with the dual-cell sensor 62, there is a case where oxygen in exhaust gas is not completely removed by the upstream-side cell 62D1 and oxygen is slightly included in exhaust gas toward the downstream-side cell 62D2. Therefore, by applying the control system or method according to the invention to the engine including the dual-cell sensor 62, it is possible to accurately detect the concentration of SOx.

In addition, the engine 10 to which the embodied system is applied is a gasoline engine; however, the control system or method according to the invention may also be applied to a diesel engine.

The embodied system uses a method of keeping the operating state of the engine 10 at the start timing of the sweep process up to the completion timing of the sweep process as control for keeping the air-fuel ratio (the concentration of oxygen) in exhaust gas during the sweep process at a constant value (stabilizing control) (see step 1015 in FIG. 10). With this method, it is not necessarily required to momentarily acquire the air-fuel ratio of exhaust gas during the sweep process. However, the system according to the invention may control the engine 10 so that the air-fuel ratio of exhaust gas is subjected to feedback control while the air-fuel ratio of exhaust gas during the sweep process is momentarily acquired as stabilizing control. For example, the embodied system can use a method of executing feedback control over the fuel injection amount so that, after the intake air amount is determined on the basis of the required output of the engine 10, the air-fuel ratio of exhaust gas coincides with a constant value. In the case where the engine 10 is a diesel engine, the system according to the invention can use a method of adjusting the intake air amount, the EGR amount, and the like, so that, after the fuel injection amount is determined on the basis of the required output of the engine 10, the air-fuel ratio of exhaust gas coincides with a constant value as stabilizing control. In the case where the engine 10 is used in combination with a motor, or the like (for example, in the case where the engine 10 is mounted on a hybrid vehicle), the system according to the invention can use a method of compensating for an insufficient amount of output with the motor while controlling the engine 10 so that the air-fuel ratio of exhaust gas is kept at a constant value.

The system according to the invention can be configured to estimate the amount of a sulfur component (the concentration of sulfur) that is contained in fuel on the basis of the concentration of SOx in exhaust gas. The concentration of sulfur in fuel generally depends on the type, or the like, of fuel. Therefore, the concentration of SOx in exhaust gas just needs to be acquired each time fuel is supplied to the engine from the viewpoint of estimating the concentration of sulfur in fuel.

What is claimed is:

1. A control system for an internal combustion engine including a limiting current sensor that is configured to detect a concentration of oxygen in exhaust gas, the control system comprising:
    an electronic control unit configured to:
    (i) detect a concentration of SOx in exhaust gas;
    (ii) control the internal combustion engine such that the concentration of oxygen in exhaust gas is kept at a constant value;
    (iii) execute a sweep process for gradually reducing a voltage, the voltage being applied to the limiting current sensor from a first voltage to a second voltage, sulfur being produced as a result of reduction of SOx in the limiting current sensor and being accumulated in the limiting current sensor at the first voltage, sulfur in the limiting current sensor being oxidized into SOx at the second voltage;
    (iv) acquire an extreme value of an output current of the limiting current sensor during execution of the sweep process from output currents of the limiting current sensor while a voltage included in a specific voltage range is applied to the limiting current sensor, the extreme value being predicted to be output based on the concentration of oxygen having the constant value in the specific voltage range; and
    (v) detect the concentration of SOx in exhaust gas based on the extreme value and a reference value, the reference value being a value of limiting current of the limiting current sensor, the value of limiting current of the limiting current sensor corresponding to the concentration of oxygen having the constant value.

2. The control system according to claim 1, wherein
    the second voltage coincides with a voltage that is used when the concentration of oxygen in exhaust gas is detected, and
    the electronic control unit is configured to, as the reference value, use a value of output current of the limiting current sensor at timing at which the voltage that is applied to the limiting current sensor is reduced to the second voltage in the sweep process.

3. The control system according to claim 1, wherein
    the electronic control unit is configured to prestore a correlation between the concentration of oxygen in exhaust gas and the value of limiting current, and
    the electronic control unit is configured to, as the reference value, use a value of limiting current, which is obtained by applying the concentration of oxygen having the constant value to the correlation.

4. The control system according to claim 1, wherein the second voltage coincides with a lower limit value of the specific voltage range.

5. A control method for an internal combustion engine including a limiting current sensor and an electronic control unit, the limiting current sensor is configured to detect a concentration of oxygen in exhaust gas, the control method comprising:
    detecting, by the electronic control unit, a concentration of SOx in exhaust gas;
    controlling, by the electronic control unit, the internal combustion engine such that the concentration of oxygen in exhaust gas is kept at a constant value;
    executing, by the electronic control unit, a sweep process for gradually reducing a voltage, the voltage being applied to the limiting current sensor from a first voltage to a second voltage, sulfur being produced as a result of reduction of SOx in the limiting current sensor and being accumulated in the limiting current sensor at the first voltage, sulfur in the limiting current sensor being oxidized into SOx at the second voltage;
    acquiring, by the electronic control unit, an extreme value of an output current of the limiting current sensor during execution of the sweep process from output currents of the limiting current sensor while a voltage included in a specific voltage range is applied to the limiting current sensor, the extreme value being predicted to be output based on the concentration of oxygen having the constant value in the specific voltage range; and
    detecting, by the electronic control unit, the concentration of SOx in exhaust gas based on the extreme value and a reference value, the reference value being a value of limiting current of the limiting current sensor, the value of limiting current of the limiting current sensor corresponding to the concentration of oxygen having the constant value.

* * * * *